United States Patent
Madabhushi et al.

(10) Patent No.: US 10,528,848 B2
(45) Date of Patent: Jan. 7, 2020

(54) HISTOMORPHOMETRIC CLASSIFIER TO PREDICT CARDIAC FAILURE FROM WHOLE-SLIDE HEMATOXYLIN AND EOSIN STAINED IMAGES

(71) Applicant: Case Western Reserve University, Cleveland, OH (US)

(72) Inventors: Anant Madabhushi, Shaker Heights, OH (US); Jeffrey John Nirschl, Philadelphia, PA (US); Andrew Janowczyk, East Meadow, NY (US); Eliot G. Peyster, Philadelphia, PA (US); Michael D. Feldman, Wilmington, DE (US); Kenneth B. Margulies, Villanova, PA (US)

(73) Assignee: Case Western Reserve University, Cleveland, OH (US)

(*) Notice: Subject to any disclaimer, the term of this patent is extended or adjusted under 35 U.S.C. 154(b) by 249 days.

(21) Appl. No.: 15/799,129

(22) Filed: Oct. 31, 2017

(65) Prior Publication Data
US 2018/0129911 A1 May 10, 2018

Related U.S. Application Data

(60) Provisional application No. 62/417,458, filed on Nov. 4, 2016.

(51) Int. Cl.
*G06K 9/00* (2006.01)
*G06K 9/62* (2006.01)
(Continued)

(52) U.S. Cl.
CPC ......... *G06K 9/6256* (2013.01); *G06K 9/2054* (2013.01); *G06K 9/6277* (2013.01);
(Continued)

(58) Field of Classification Search
CPC .................................................. G06K 9/6256
See application file for complete search history.

(56) References Cited

PUBLICATIONS

Litjens, et al. "Deep Learning as a Tool for Increased Accuracy and Efficiency of Histopathological Diagnosis." Scientific Reports | 626286 | DOI: 10.1038/srep26286. Published on May 23, 2016.
(Continued)

*Primary Examiner* — Stephen P Coleman
(74) *Attorney, Agent, or Firm* — Eschweiler & Potashnik, LLC

(57) ABSTRACT

Methods, apparatus, and other embodiments predict heart failure from WSIs of cardiac histopathology using a deep learning convolutional neural network (CNN). One example apparatus includes a pre-processing circuit configured to generate a pre-processed WSI by downsampling a digital WSI; an image acquisition circuit configured to randomly select a set of non-overlapping ROIs from the pre-processed WSI, and configured to provide the set of non-overlapping ROIs to a deep learning circuit; a deep learning circuit configured to generate an image-level probability that a member of the set of non-overlapping ROIs is a failure/abnormal pathology ROI using a CNN; and a classification circuit configured to generate a patient-level probability that the patient from which the region of tissue represented in the WSI was acquired is experiencing failure or non-failure based, at least in part, on the image-level probability.

20 Claims, 9 Drawing Sheets

(51) Int. Cl.
*G06N 3/08* (2006.01)
*G06N 3/04* (2006.01)
*G06T 3/40* (2006.01)
*G06K 9/20* (2006.01)
*G16H 50/20* (2018.01)

(52) U.S. Cl.
CPC ............. *G06N 3/0472* (2013.01); *G06N 3/08* (2013.01); *G06T 3/40* (2013.01); *G16H 50/20* (2018.01); *G06T 2207/10024* (2013.01); *G06T 2207/20076* (2013.01); *G06T 2207/30048* (2013.01)

(56) References Cited

PUBLICATIONS

Gho, et al. "High Resolution Systematic Digital Histological Quantification of Cardiac Fibrosis and Adipose Tissue in Phospholamban p.Arg14del Mutation Associated Cardiomyopathy." PLOS ONE, Apr. 2014, vol. 9, Issue 4. Published Apr. 14, 2014.

| Metric | Random Forest | Deep Learning | p value |
|---|---|---|---|
| Image-level results | | | |
| Accuracy | 0.871±0.01 | 0.946± 0.01 | < 0.001 |
| Sensitivity | 0.883±0.02 | 0.968± 0.02 | 0.01 |
| Specificity | 0.860±0.01 | 0.927± 0.01 | 0.01 |
| Positive Predictive Value | 0.847±0.01 | 0.921± 0.01 | < 0.001 |
| AUC | 0.935±0.001 | 0.977±0.01 | < 0.001 |
| Patient-level results | | | |
| Accuracy | 0.917±0.01 | 0.962±0.01 | 0.002 |
| Sensitivity | 0.932±0.03 | 0.993±0.01 | 0.033 |
| Specificity | 0.905±0.03 | 0.935±0.01 | n.s. |
| Positive Predictive Value | 0.896±0.02 | 0.93±0.01 | n.s. |
| AUC | 0.960±0.01 | 0.989±0.01 | 0.002 |

HISTOMORPHOMETRIC CLASSIFIER TO PREDICT CARDIAC FAILURE FROM WHOLE-SLIDE HEMATOXYLIN AND EOSIN STAINED IMAGES

CROSS REFERENCE TO RELATED APPLICATIONS

This application claims the benefit of U.S. Provisional Application 62/417,458 filed Nov. 4, 2016.

FEDERAL FUNDING NOTICE

The invention was made with government support under grants 1U24CA199374-01, R01CA202752-01A1, R01CA208236-01A1, R21CA179327-01, R21CA195152-01, R01DK098503-02, R01HL105993, F30NS092227, and 1 C06 RR012463-01 awarded by the National Institutes of Health. Also grants W81XWH-13-1-0418, W81XWH-14-1-0323, and W81XWH16-1-0329 awarded by the Department of Defense. The government has certain rights in the invention.

BACKGROUND

Cardiovascular diseases are the leading cause of death globally, and the leading cause of hospital admissions in the U.S. and Europe. More than 26 million people worldwide suffer from heart failure each year, and about half of these patients die within five years. Clinical heart failure is a progressive syndrome where impaired ventricular function results in inadequate systemic perfusion. The diagnosis of heart failure conventionally relies on clinical history, physical examination, basic lab tests, and imaging. This diagnostic rubric has not changed in three decades, and lacks the ability to accurately sub-classify patients into the numerous potential clinical etiologies, which in turn has limited the development of new treatments. However, when the cause of heart failure is unidentified, endomyocardial biopsy (EMB) represents the gold standard for evaluation and grading of heart disease.

Conventional approaches to analyzing EMBs are not optimal. Manual interpretation of EMB suffers from high inter-rater variability in the pathologic diagnosis of heart disease. Manual interpretation of EMBs by expert human pathologists has an accuracy of only approximately 75% when classifying an EMB as indicating heart failure or non-heart failure. Furthermore, manual interpretation of EMB has limited clinical indications. Meanwhile, the increasingly common digitization of glass pathology slides has lead to a proliferation of whole-slide imaging (WSI) platforms.

Conventional image analysis approaches that employ digitized WSI images may involve manually engineering features. The manually engineered features may include intensity statistics, texture descriptors, or image decompositions. These features are then provided to a supervised machine learning algorithm for classification or regression. Designing discriminative features is a long process that requires computational experience and domain knowledge to develop features that might, potentially, be relevant to the intended classification. Furthermore, designing discriminative features may leave out relevant or even currently biologically unknown features.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
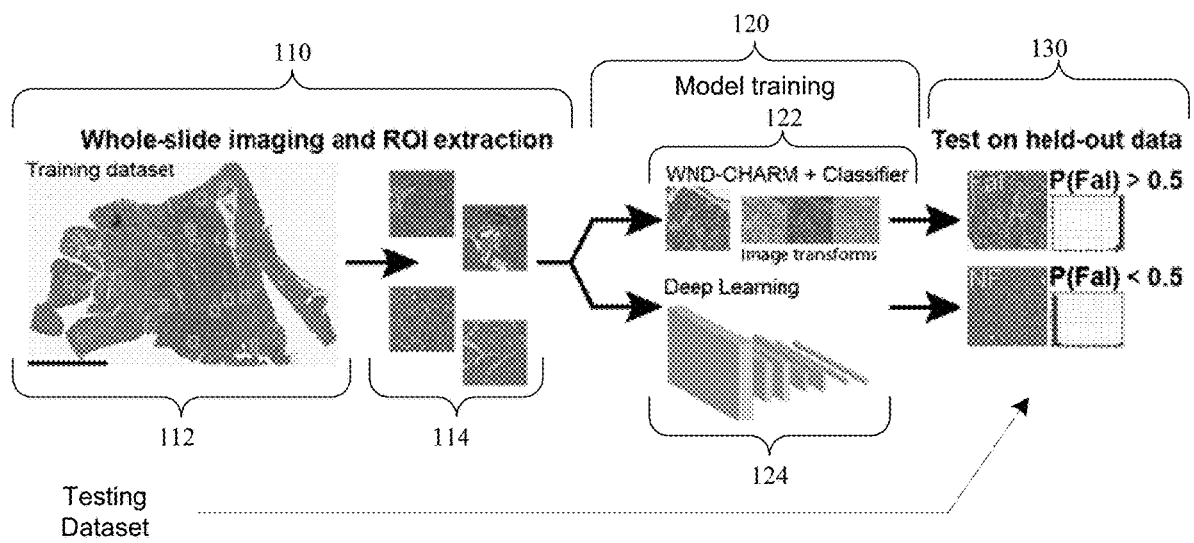
FIG. 1 illustrates a schematic overview of a digital pathology workflow to predict heart failure.

Embodiments described herein train and employ a deep learning convolutional neural network (CNN) classifier to predict clinical heart failure from digitized hematoxylin and eosin (H&E) stained whole slide images (WSIs) of heart tissue. Embodiments described herein facilitate the automatic identification of cardiovascular pathology from WSIs of cardiovascular histopathology, including tissue derived from heart transplants, explants, surgical tissue samples, EMBs, or other diagnostic cardiac biopsies. Quantitative histomorphometry involves the conversion of a digitized histopathology slide into a series of quantitative measurements of tissue morphology. Example embodiments facilitate directly transforming a digitized WSI of heart tissue into a probability of a patient-level diagnosis. Example methods and apparatus automatically and reproducibly quantify the extent of cardiovascular pathology in a WSI, whether due to ischemic causes, non-ischemic causes, or other causes. Example methods and apparatus use an automated computational histomorphometric image analysis to facilitate a patient-level prediction of clinical heart failure or heart disease based on sub-visual features extracted from cardiac histopathology WSIs with an accuracy of at least 96.2%. Example methods and apparatus are more accurate in predicting heart failure than conventional feature-engineering approaches, and are also more accurate than expert human pathologists. Example methods and apparatus facilitate automated and reproducible classification of WSIs because the CNN is deterministic and will repeatedly produce the same classification on the same input sample, in contrast to human experts that exhibit inter-expert and intra-expert variances. Automated analysis and grading of cardiac histopathology as described herein may further be employed as an objective second read of EMBs to improve heart disease characterization and detection. Example embodiments detect tissue-level pathology, and facilitate the timely re-examination of clinically normal patients who may subsequently be found to have severe tissue pathology that was otherwise undetected by conventional approaches. Embodiments described herein may further predict immune-mediated transplant rejection based, at least in part on a CNN's analysis of cardiovascular histopathology. Example embodiments facilitate deep-phenotyping to support precision medicine initiatives to enhance the targeting of therapeutics based on the deeper understanding of disease mechanisms and their manifestations within individual patients.

Conventionally, deep learning CNNs have not been applied to image analysis of cardiac histopathology represented in WSIs. Deep learning is an example of representation learning, which is a class of machine learning approaches in which discriminative features are not engineered or pre-specified, but are instead learned by the machine learning classifier directly from raw data. In a typical CNN, there are multiple artificial neurons, or nodes (also referred to as parameters), arranged in a hierarchical network of successive convolutional, max-pooling, and fully-connected layers. The hierarchical network structure facilitates the CNN model to approximate complex functions and learn non-linear feature combinations that maximally discriminate among the classes. The approximation of complex functions may occur as a result of each layer being a higher level abstraction than the previous layer, where, for example, an earlier layer learns pixel-level features, while later levels combine the lower level features into more complex objects or concepts. When a CNN model is trained on a sufficiently large data set, the CNN model may generalize to unseen examples from a population.

Embodiments described herein employ a modified deep learning CNN classifier that provides superior performance to conventional approaches that employ human engineered features in a WND-CHARM+RF pipeline or even conventional CNNs. As used herein, WND-CHARM refers to "Weighted Neighbor Distances using a Compound Hierarchy of Algorithms Representing Morphology". RF refers to a random forests classifier. Example methods and apparatus provide superior performance than conventional approaches due, at least in part, to the learning of novel discriminative features or nonlinear feature combinations that are not present in the WND-CHARM+RF pipeline, and to the improved efficiency and performance of the modified CNN architecture described herein.

In one embodiment, a population includes 209 patients divided into two cohorts. A first cohort includes patients with end-stage heart failure (Failing or Fal, N=96) and a second cohort includes a comparison group of patients without known heart failure (Non-Failing or NF, N=113). Tissue from the failing cohort is obtained at the time of cardiac explantation for transplant, or as core samples obtained at the time of left ventricular assist device (LVAD) implantation. The failing cohort includes patients with clinically diagnosed ischemic cardiomyopathy (ICM) or idiopathic dilated cardiomyopathy (NICM). Organ donors without a history of heart failure comprise the NF cohort. In this embodiment, WSIs are generated by H&E staining formalin-fixed, paraffin-embedded transmural left ventricular free wall sections from each heart then digitizing the sections at 20× magnification. WSIs may be acquired, in one example, using an Aperio ScanScope slide scanner, or other WSI scanner. The images are down-sampled to 5× magnification for image analysis. Down-sampling to 5× magnification facilitates expert human assessment of tissue pathology. For example, an apparent magnification of 5× facilitates the identification by expert pathologists of macroscopic (tissue level) and microscopic (cellular level) pathology in a given ROI. An apparent magnification of 5× further facilitates efficient automated image analysis.

In this embodiment, the population of patients is randomly split into two datasets: a first cohort of 104 patients was designated for training, and a separate cohort of 105 patients was held out as an independent test set. The training dataset was further split at the patient level into three-folds for cross-validation to assess training and validate parameters or properties of the CNN. For a patient's WSI image in both datasets, eleven non-overlapping regions of interest (ROI) were extracted randomly from with the tissue border of the WSI. An ROI in this example has an area of 2500 µm$^2$. Randomly extracting non-overlapping ROIs from the tissue area facilitates the sampling of the extent of disease present throughout the tissue sample. In this embodiment, eleven non-overlapping ROIs are used so that a voting-based scheme will yield a majority vote with no ties for a binary classifier. Thus, an individual ROI will yield an image-level prediction (e.g., disease v. no disease, failing v. non-failing) and a final, patient-level prediction may be determined by a majority prediction (e.g. majority vote) from the individual ROIs. Stain normalization may be applied to a WSI and ROIs may be extracted before stain normalization (raw) and after stain normalization (normalized) to assess the need for stain normalization in cardiac histopathology. Stain normalization may be, for example, Macenko stain normalization or other type of stain normalization. In a preferred embodiment, no stain normalization is employed. The set of training images are used to build independent classifiers to predict heart failure. In a preferred embodiment, the independent classifier is built using a deep learning approach that requires no image segmentation. For testing and comparison purposes, a WND-CHARM classifier that uses conventional feature engineering coupled with a random decision forest classifier was built.

FIG. 1 is a schematic overview of a digital pathology workflow to predict heart failure suitable for use by embodiments described herein. At 110, a set of patients are divided into a training dataset and a test dataset. WSIs 112 acquired from the set of patients are scanned and ROIs 114 are extracted for image analysis. In this example, all ROIs from the same patient were given the same label which was determined by whether the patient had clinical or pathological evidence of heart disease. For example, an ROI may be labeled as "disease or no disease", or "failing or non failing". FIG. 1 illustrates a workflow that includes two different approaches 120 to model training. FIG. 1 illustrates, at a first point 122, training a conventional engineered feature classifier, for example a WND-CHARM+RF classifier. FIG. 1 further illustrates, at a second point 124, training a naïve deep learning CNN classifier as claimed and described herein. Three-fold cross validation was used to train and test both the conventional heart failure classifier 122 and the preferred deep learning CNN embodiment 124. The trained models were then evaluated at 130 at both the image level and the patient-level on a held-out test dataset. In this example, a probability of failure p(Fal)>0.5 results in a classification of failure.

A conventional feature engineering approach may employ, for example, WND-CHARM+RF to compute image features for a patient ROI. In this example, the WND-CHARM-based conventional approach computed 4059 image features for each patient ROI. The top 20 WND-CHARM features were then selected using a minimum redundancy, maximum relevance approach, and the top 20 most discriminative features were then input to a random decision forest (RF) classifier. The RF classifier was used to calculate a per-ROI (e.g. image-level) probability of heart failure, which was thresholded at 0.5. A per-ROI probability of heart failure greater than 0.5 indicated failure, while a per-ROI probability of heart failure less than 0.5 indicated non-failure. The fraction of ROIs as failing gave the patient-level probabilities.

Example embodiments improve on conventional approaches by using deep learning to predict clinical heart failure using only the input images without requiring feature crafting. In one embodiment, the deep learning model uses a modified AlexNet architecture. A conventional AlexNet CIFAR 10 architecture accepts a 32×32 pixel input. Other AlexNet configurations accept input sizes of 225 pixels by 225 pixels. Example embodiments employ a modified network that accepts 64×64 pixel RGB image patches (having an area of 128 $\mu m^2$) with a label corresponding to the cohort to which the patient from which the image patch was acquired belongs. (e.g. failing, non-failing). A 64×64 pixel input size provides an optimized balance of speed and accuracy compared to a 32×32 pixel approach which is less accurate, and compared to input sizes greater than 64×64 pixels that do not significantly improve accuracy but increase the time required to process.

Example embodiments further reduce the number of nodes (also referred to as parameters or neurons) employed in the network while achieving similarly accurate performance but with a significant reduction in training time compared to conventional approaches. For example, a conventional AlexNet CIFAR CNN architecture employs over 145 thousand parameters (e.g. nodes, neurons) while example embodiments employ approximately 13 thousand parameters, which is nearly an order of magnitude reduction in the number of neurons or parameters employed. Reducing the number of nodes reduces the training time required to train the CNN compared to conventional approaches, and further reduces the computational complexity of analyzing an image with the CNN, which in turn reduces the energy and computational resources required to operate the CNN or a CADx system that employs the CNN. For example, embodiments described herein reduce the amount of data required to train the system. The larger the number of parameters, the larger the number of patients/samples required before the system can be trained to generalized well. This is problematic in a medical domain where it is impractical or difficult, if indeed possible, to acquire the millions of exemplars that may be obtained from social media in the facial recognition or language detection domains. By reducing the amount of data required to train the CNN, example embodiments thus improve on conventional approaches.

Additionally, example embodiments employ a fully-convolutional network, in which the max-pooling layers and fully connected layers employed in conventional neural networks are replaced by convolutional layers, facilitating image-level predictions (e.g. producing output images) significantly faster than conventional approaches. In one embodiment, the deep learning classifier is trained using one-hundred patches per ROI, per patient. The training set is further augmented by rotating each patch by 90 degrees. Embodiments may apply additional numbers of rotations, or rotations of different numbers of degrees, to patches. In this example, each fold of the three-fold cross validation was trained using NVIDIA DIGITS and Caffe for 30 epochs on a Titan X GPU, with CUDA 7.5 and cuDNN, and optimized by stochastic gradient descent with a fixed batch size of 64. DIGITS facilitates the viewing of results, while Caffe is employed for processing. Embodiments described herein may conduct image processing and analysis using, for example, MATLAB version R2015 or newer, Python, or Caffe, or may employ other image processing and analysis packages. While 30 epochs are used in this example, other numbers of epochs may be employed.

Figure 2:
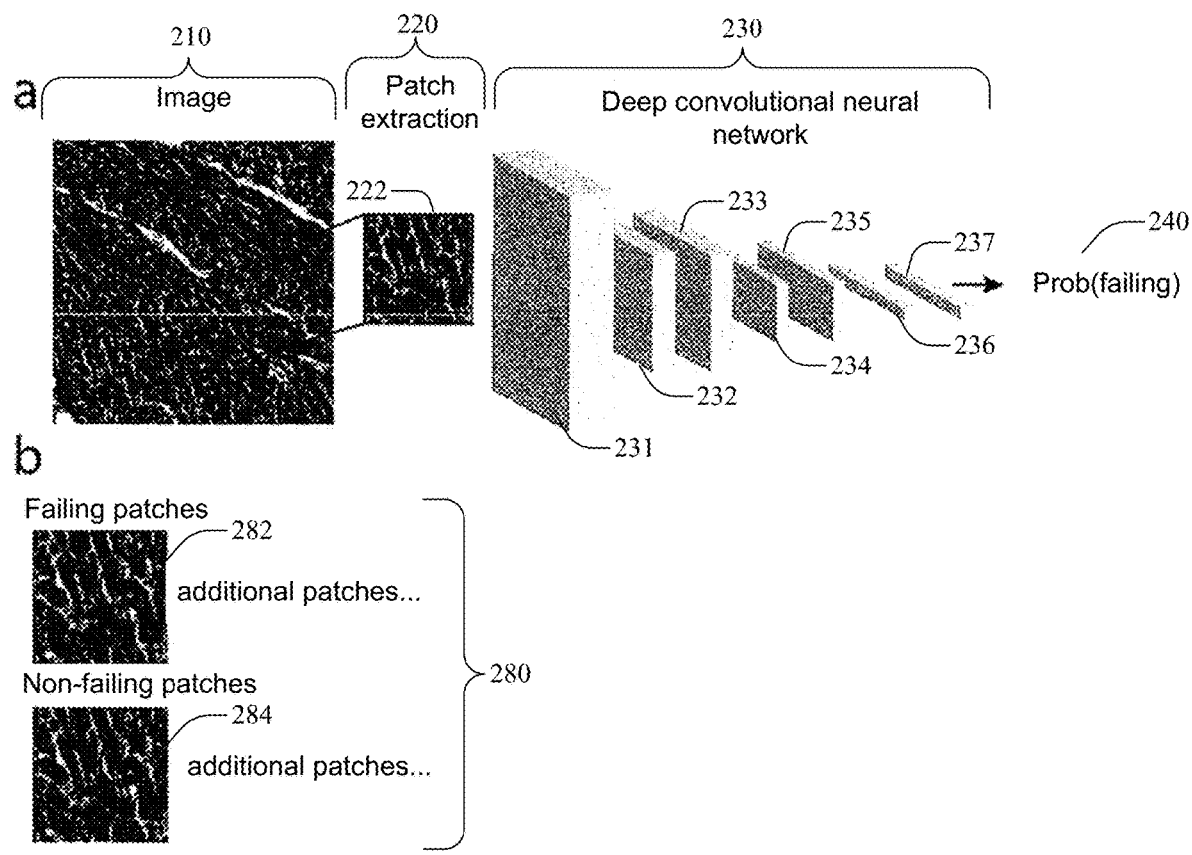
FIG. 2 illustrates an example deep learning architecture for heart failure classification.

FIG. 2 illustrates an example embodiment of a deep learning architecture 200 for heart failure classification that may be employed by example embodiments. Deep learning architecture 200 is suitable use with methods and apparatus described herein, including apparatus 500, method 600, method 700, or method 800. An image 210 of an ROI is accessed. The image 210 is, in this example, a digitized H&E WSI of an ROI of heart tissue. The digitized WSI may be a red-green-blue (RGB) WSI. In another embodiment, the digitized WSI may be a grayscale WSI, another color space (e.g., HUV) WSI, or other type of WSI. A plurality of patches are extracted 220 from the image 210. In this example, only one patch 222 is illustrated for clarity. Recall that in one embodiment, one-hundred patches are extracted from an ROI. By sub-sampling one hundred 64×64 pixel patches from an ROI, example embodiments augment the data used by the CNN by increasing the diversity of inputs presented to the CNN. For example, a given 256 by 256 pixel image with disease should produce a "disease" prediction (e.g. failure) regardless of where the 64 by 64 pixel sub-patch is selected from within the image. By randomly sub-sampling patches from an ROI, example embodiments improve on conventional approaches by both increasing the number N of inputs available to the CNN, while also training the CNN to be insensitive to minor image transforms (e.g., translations). In other embodiments, other numbers of patches greater than one-hundred or less than one-hundred may be extracted. Sampling fewer patches may not represent the entire area from an ROI. Sampling more patches introduces redundancies in which patches overlap and become highly correlated (e.g. the same patch shifted by one pixel), and more patches will further prolong training time. In one embodiment, the number of patches extracted from the ROI may be user adjustable. In one embodiment, patches are rotated ninety degrees to further augment the training data set. In another embodiment, patches may be rotated other numbers of degrees, for example, one degree, two degrees, 45 degrees, 180 degrees, or 270 degrees.

Patch 222 is provided as input to a deep learning CNN 230. Embodiments described herein may employ a deep learning CNN that includes convolutional layers 231-237. In this example, each convolutional layer of CNN 230 contains a rectified linear activation unit (ReLu) as well as batch normalization. Batch normalization corrects covariate shift between layers of the network. Covariate shift may be defined as a change in the distribution of a function's domain. Covariate shift may complicate the training of a CNN. In this embodiment, the CNN is composed of alternating convolutional, activation, and batch normalization layers. In one embodiment, an activation layer may include a ReLu through which a weighted sum of the inputs from the previous layer may be passed. The ReLu is a non-linear function. In another embodiment, the activation layer may employ other, different non-linear functions. Table 1 below describes one embodiment of a CNN suitable for use by embodiments described herein.

TABLE 1

| Layer | Kernel | Stride | Number Of Kernels |
|---|---|---|---|
| Input | 64 × 64 | | |
| Conv1a | 3 | 1 | 16 |
| Bn1a | | | |
| Relu1a | | | |
| Conv1b | 2 | 2 | 16 |
| Bn1b | | | |
| Relu1b | | | |
| Conv2a | 3 | 1 | 16 |
| Bn2a | | | |
| Relu2a | | | |
| Conv2b | 3 | 2 | 16 |
| Bn2b | | | |
| Relu2b | | | |
| Conv3a | 3 | 1 | 16 |
| Bn3a | | | |
| Relu3a | | | |
| Conv3a | 4 | 2 | 16 |
| Bn3a | | | |
| Relu3a | | | |
| Fc-8-conv | 5 | | 2 |

The CNN described by table 1 includes seven layers. In this example, input includes at least one 64 pixel by 64 pixel patch. The 64 pixel by 64 pixel patch may be extracted from an RGB image, a grayscale image, a hue-saturation-value (HSV) image, a color deconvoluted image, or an immuno-histochemistry (IHC) image, including a WSI. A first convolutional layer (conv1a) has a kernel of size 3, a stride of 1, and an output of 16 kernels (3, 1, 16). The kernel value indicates the number of filters at that layer. The stride indicates how the kernel convolves about the input: a stride of one indicates a one-pixel shift. Subsequent convolutional layers include conv1b(2, 2, 16), conv2a(3, 1, 16), conv2b(3, 2, 16), conv3a(3, 1, 16), and conv3b(4, 2, 16). The fully connected layer Fc-8-conv has a stride of size 5 and an output of 2. The fully connected layer Fc-8-conv's output of 2 indicates a probability that the input is failing or non-failing. The fully connected layer Fc-8-conv may be a convolutional layer having a kernel exactly the size of the previous layer. Fully connected layer Fc-8-conv thus acts like a fully connected layer, but has improved numerical properties. In other embodiments, other numbers of layers may be employed. In other embodiments, layers may have different kernels, different strides, and different outputs.

CNN 230 produces an output 240 that represents a probability that the patch 222 is a failing patch. FIG. 2 further illustrates an example set of training patches 280. The set of training patches 280 includes a set of failing patches 282, and a set of non-failing patches 284. The set of training patches 280 is used to train or test the deep learning CNN 230.

Embodiments described herein train a CNN using k-cross validation. Cross-validation is a technique to measure how a classifier will generalize outside the training dataset. The original training data set is split into k non-overlapping groups of patients, where k is an integer. In one embodiment, the original training data set is split into three non-overlapping groups of patients. The first k−1 groups (in this example, two) are used to train the CNN and the remaining group is used to test to CNN. No patient is ever in the training group and the test group at the same time. This process is repeated k times until all the patients in the original training data set have been used for training and testing, but never at the same time. In one embodiment, training the CNN may include using backpropagation to compute the gradient of an objective function. In another embodiment, other techniques for finding the minima of the objective function may be employed.

Embodiments described herein may detect tissue pathology even in patients without diagnosed pre-existing heart failure or pathology. For example, a patient without clinically diagnosed pre-existing heart failure may be predicted as failing with a very high probability by a CNN at both the image-level and at the patient-level. In this example, the non-failing patient, while without heart failure, has severe or occult tissue pathology that was undetected by conventional diagnostic techniques. The severe tissue pathology may be predictive of future heart failure. Thus, embodiments described herein may classify a patient as either non-failing or "abnormal or failing". Classifying a patient as "failure/abnormal" that may otherwise be deemed a false positive provides the additional benefit of directing resources in a timely manner to patients that may go untreated until conventionally detectable symptoms develop.

Figure 3:
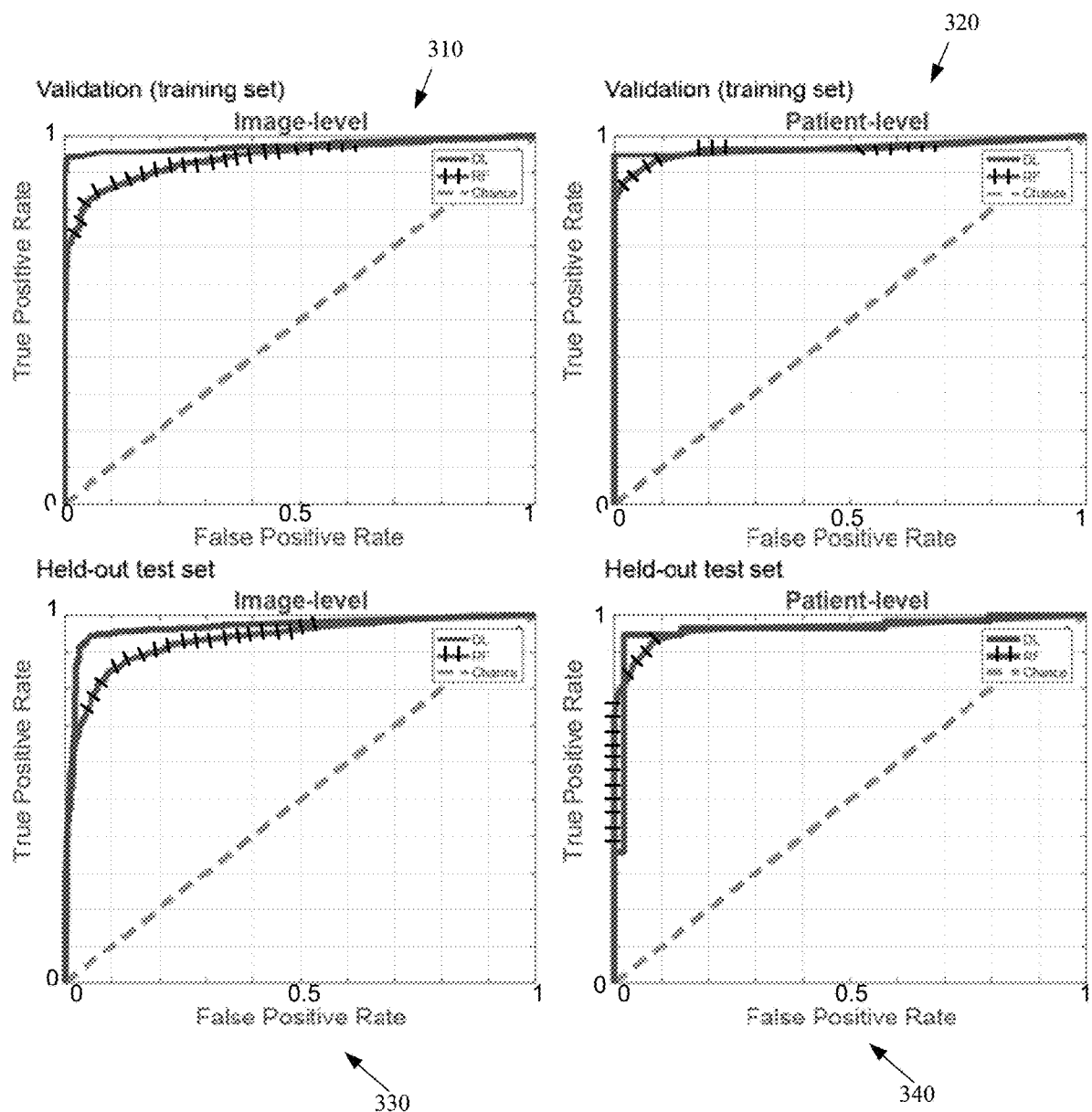
FIG. 3 illustrates receiver operator characteristic (ROC) curves for detection of clinical heart failure or severe tissue pathology

FIG. 3 illustrates graphs of the receiver operator characteristic (ROC) curves for the detection of clinical heart failure or severe tissue pathology. The vertical axes represent the true positive rate, and the horizontal axes represent the false positive rate. In graphs 310, 320, 330, and 340, the solid line represents the deep learning ROC curve, the barred line represents the conventional WND-CHARM+RF ROC curve, and the dashed line represents chance or mere guessing.

Graph 310 illustrates the ROC curve for image-level detection on a training data set. Graph 310 illustrates the ROCs of DL embodiments described herein vs. conventional RF approaches. In graph 310, p<0.0001, using a two-sample Kolmogorov-Smirnov (KS) test, where p represents the p-value.

Graph 320 illustrates the ROC curves for patient-level detection on the training data set. Graph 320 represents the ROCs of deep learning embodiments described herein (DL) vs. conventional WND-CHARM+RF (RF) approaches, also using a two-sample KS test.

Graph 330 represents the ROC of deep learning embodiments described herein (DL) vs. conventional WND-CHARM+RF (RF) approaches for image-level detection on a held-out test data set. In graph 330, p<0.0001, and a two-sample KS test was also used.

Graph 340 represents the ROC of deep learning embodiments described herein (DL) vs. conventional WND-CHARM+RF (RF) approaches for patient-level detection on the held-out test data set. In graph 340, a two-sample KS test was also used. FIG. 3 thus provides evidence of the improved accuracy of example embodiments compared to conventional approaches for predicting heart failure.

Figure 4:
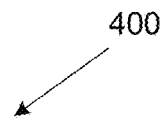
FIG. 4 illustrates image-level and patient-level results for different approaches to detecting clinical heart failure or severe tissue pathology.

FIG. 4 illustrates a table 400 of patient-level performance evaluation for predicting clinical heart failure or severe tissue pathology from H&E stained digitized WSIs for a held-out test set. The results presented in table 400 represent the mean+−SD of three models. Each of the three models was trained on 770 images acquired from 70 patients. The three models were evaluated on the held-out test set of 105 patients. The patient-level diagnosis is a majority vote over all the images (e.g. ROIs) from a single patient. Statistics presented in table 400 were determined by an unpaired two-sample t-test with an N of three folds. The "Random Forest" column indicates the results of a WND-CHARM+RF approach to predicting heart failure. The "Deep Learning" column indicates the results of the deep learning CNN approach employed by embodiments described herein. On every metric, the deep learning (e.g. CNN) approach outperforms the conventional engineered features random forest approach. For example, the AUC for image-level results for the conventional WND-CHARM+RF approach is 0.935+−0.001, while the AUC for image level results for example embodiments is 0.977+−0.01. Similarly, the AUC for patient-level results for the conventional WND-CHARM+RF approach is 0.960+−0.01, while the AUC for patient-level results for example embodiments is 0.989+−0.01. Thus, FIG. 4 provides evidence of the improved accuracy of example embodiments compared to conventional technologies for predicting heart failure.

Example methods and apparatus thus demonstrably improve on conventional technologies for predicting clinical heart failure. For example, methods and apparatus described herein predict clinical heart failure or severe tissue pathology with an average area under the curve (AUC) accuracy of at least 0.977, compared with conventional approaches that achieve an average AUC of only 0.935. Example embodiments further improve on the performance of expert human pathologists in predicting heart failure or sever tissue pathology, in that expert human pathologists typically achieve an individual accuracy of only 75% at the patient level with a Cohen's kappa inter-rate agreement of 0.40. By increasing the accuracy with which clinical heart failure or severe tissue pathology is predicted, example methods and apparatus produce the concrete, real-world technical effect of increasing the probability that at-risk patients receive timely treatment tailored to the particular pathology they exhibit. The additional technical effect of reducing the expenditure of resources and time on patients who have a less aggressive pathology is also achieved. Example embodiments further improve on conventional approaches by providing a more accurate second reader to facilitate the reduction of inter-reader variability among human pathologists. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 5:
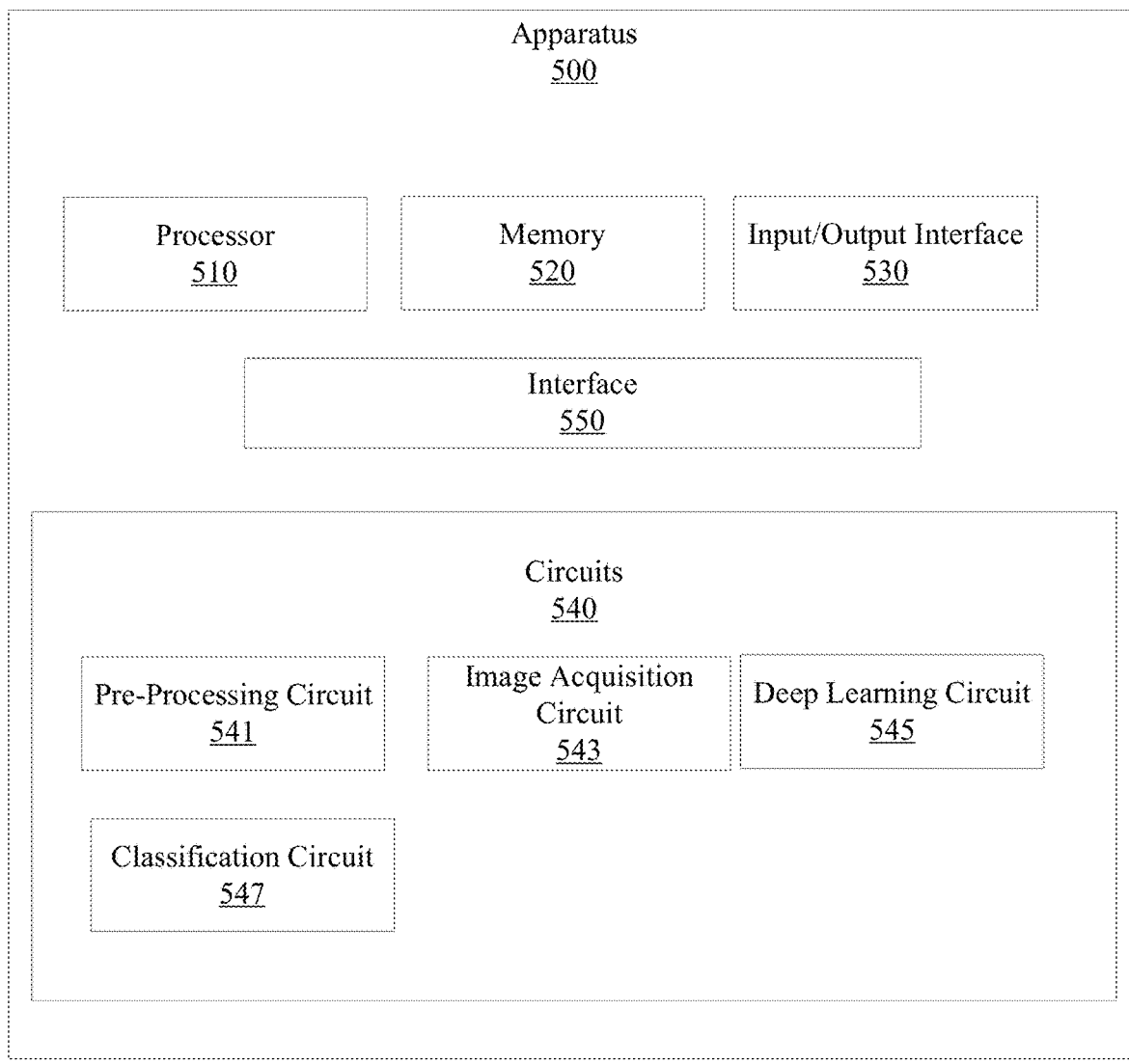
FIG. 5 illustrates an example apparatus that predicts heart failure.

FIG. 5 illustrates an example apparatus 500 that predicts clinical heart failure. Apparatus 500 includes a processor 510, a memory 520, an input/output interface 530, a set of circuits 540, and an interface 550 that connects the processor 510, the memory 520, the input/output interface 530, and the set of circuits 540. The set of circuits 540 includes a pre-processing circuit 541, an image acquisition circuit 543, a deep learning circuit 545, and a classification circuit 547.

Memory 520 is configured to store a digitized whole slide image (WSI) of a region of tissue. The region of tissue may be, for example, a section of tissue demonstrating heart failure pathology, and thus the WSI may be of cardiovascular histopathology. The digitized WSI may be an RGB image, a grey scale image, or other color space image. The digitized WSI has a plurality of pixels. A pixel in the digitized WSI has an intensity or a color value. In one embodiment, the volume illustrated in the digitized WSI represents tissue collected from a patient with clinically diagnosed ischemic cardiomyopathy (ICM), or idiopathic dilated cardiomyopathy (NICM), or other heart disease related pathology. The tissue may be collected from a patient who received a heart transplant or a LVAD. In one embodiment, the image may be acquired from an organ donor without a history of heart failure. The digitized WSI may represent tissue derived from a transplant, an explant, a surgical tissue sample, an EMB, or other surgical or biopsy procedure. In other embodiments, the volume illustrated in the image may be associated with other imaging systems, or be of other regions demonstrating other types of pathology.

Pre-processing circuit 541 is configured to generate a pre-processed WSI. Pre-processing circuit 541 may generate the pre-processed WSI by downsampling the digital WSI. For example, in one embodiment, the WSI is acquired at a 20× magnification. Generating the pre-processed WSI may include downsampling the digital WSI to an apparent magnification of 5×. In another embodiment, the WSI may be acquired at another, different magnification, or the WSI may be downsampled to another, different apparent magnification. In another embodiment, pre-processing the WSI may include color normalization, or determining where in the slide the tissue sample is located.

Image acquisition circuit 543 is configured to randomly select a set of non-overlapping ROIs from the pre-processed WSI. Image acquisition circuit 543 provides the set of non-overlapping ROIs to the deep learning circuit 545. In this embodiment, a member of the set of non-overlapping ROIs has dimensions of 256 pixels by 256 pixels. The set of non-overlapping ROIs has an odd cardinality. In one embodiment, the set of non-overlapping ROIs extracted by image acquisition circuit 543 includes eleven non-overlapping ROIs. Selecting or accessing an ROI from the WSI includes acquiring electronic data, reading from a computer file, receiving a computer file, reading from a computer memory, or other computerized activity.

Deep learning circuit 545 is configured to generate an image-level probability that a member of the set of non-overlapping ROIs is a non-failure ROI or a failure/abnormal pathology ROI. In one embodiment, deep learning circuit 545 provides the member of the set of non-overlapping ROIs to a CNN. Providing the member of the set of non-overlapping ROIs includes acquiring electronic data, reading from a computer file, receiving a computer file, reading from a computer memory, or other computerized activity. The CNN produces the image-level probability based, at least in part, on the member of the set of non-overlapping ROIs. The CNN resolves features present in the digitized WSI at a higher order or higher level than a human can resolve.

In one embodiment, the CNN is configured to accept one-hundred 64 pixel by 64 pixel input patches per member of the set of non-overlapping ROIs. In another embodiment, the CNN may be configured to accept another, different number of input patches, or to accept input patches having different dimensions. For example, the CNN may be configured to accept 32 pixel by 32 pixel input patches, or 128 pixel by 128 pixel input patches.

In one embodiment, the CNN is a seven-layer CNN. In this embodiment, the CNN has 13460 parameters (e.g., neurons, nodes). In another embodiment, the CNN may have another, different number of neurons. For example, the CNN may have 12000 neurons, or 15000 neurons.

In this embodiment, the CNN includes a first layer comprising a convolutional layer, a batch normalization layer, and an activation layer. In this embodiment, the convolutional layer has 16 kernels of size 3 and uses a stride of 1. In this embodiment, the kernel is a 3×3 matrix, with the matrix values representing the learned weights.

In this embodiment, the CNN also includes a second layer comprising a convolutional layer, a batch normalization layer, and an activation layer. In this embodiment, the convolutional layer has 16 kernels of size 2, and uses a stride of 2.

In this embodiment, the CNN also includes a third layer comprising a convolutional layer, a batch normalization layer, and an activation layer. In this embodiment, the convolutional layer has 16 kernels of size 3, with a stride of 1.

In this embodiment, the CNN also includes a fourth layer comprising a convolutional layer, a batch normalization layer, and an activation layer. In this embodiment, the convolutional layer has 16 kernels of size 3, with a stride of 2.

In this embodiment, the CNN also includes a fifth layer comprising a convolutional layer, a batch normalization layer, and an activation layer. In this embodiment, the convolutional layer has 16 kernels of size 3, with a stride of 1.

In this embodiment, the CNN also includes a sixth layer comprising a convolutional layer, a batch normalization layer, and an activation layer. In this embodiment, the convolutional layer has 16 kernels of size 4, and uses a stride of 2.

In this embodiment, the CNN further includes a fully connected layer. The fully connected layer has a kernel of 5 and an output of 2. In another embodiment, other numbers of layers, kernels, strides, or outputs may be employed.

Classification circuit 547 is configured to compute a patient-level probability that the patient from which the region of tissue represented in the WSI was acquired has failure or non-failure. Classification circuit 547 computes the patient-level probability based, at least in part, on the image-level probability. In one embodiment, the classification circuit 547 computes the patient-level probability based on a majority vote of the image-level probabilities associated with members of the set of non-overlapping ROIs. Selecting a set of non-overlapping ROIs that has an odd cardinality facilitates avoiding tie votes and thus achieving a majority vote. In this embodiment, apparatus 500 identifies a patient with heart failure with a sensitivity of 99% and a specificity of 93%.

In another embodiment, classification circuit 547 may control a computer aided diagnosis (CADx) system to classify the region of tissue represented in the WSI based, at least in part, on the probability generated by deep learning circuit 545. For example, classification circuit 547 may control a CADx system to distinguish the image based, at least in part, on the probability or the classification generated by classification circuit 547. In other embodiments, other types of CADx systems may be controlled, including CADx systems for distinguishing other types of tissue presenting other, different pathologies that may be distinguished based on features detected by deep learning circuit 545 represented in a digitized WSI. For example, embodiments described herein may be employed to classify or grade breast cancer (BCa) based on WSIs of BCa tissue. Other embodiments may be employed to classify kidney disease, or brain pathologies.

In one embodiment of apparatus 500, the set of circuits 540 further includes a training circuit configured to train the CNN. Training the CNN includes accessing a training dataset of WSIs. In one embodiment, the WSIs are acquired at 20× magnification. The training dataset includes a first subset of WSIs of tissue acquired from patients demonstrating clinically diagnosed heart failure, and a second, disjoint subset of WSIs of tissue acquired from patients that have not been clinically diagnosed with heart failure. In one embodiment, the first subset is acquired from heart failure patients receiving a heart transplant or LVAD. Tissue acquired from the first subset may be acquired post-explant, or may be acquired as surgical core samples for patients receiving LVAD. In this embodiment, the second subset is acquired from organ donors without a history of heart failure, but where the heart was not used for transplant. Members of the training dataset may be downsampled to an apparent magnification of 5×.

The training circuit is further configured to split the training dataset into k−1 groups, where k is an integer. In this embodiment, three-fold cross validation is employed. In other embodiments, other forms of cross validation may be employed by the training circuit. In one embodiment, before splitting the training dataset, a held out testing set is removed from the training dataset.

The training circuit is further configured to train the CNN with the first k−1 groups. Training the CNN includes extracting 64 pixel by 64 pixel RGB image patches from an ROI randomly selected from a member of the first k−1 groups of WSIs, where the member has a label corresponding to the cohort to which the patient from which the WSI was acquired belongs (e.g. failing or non-failing). The CNN is trained using one-hundred patches per ROI. In one embodiment, the training data set is augmented by rotating a patch by ninety degrees. In one embodiment, the CNN is trained per fold for thirty epochs using stochastic gradient descent with a fixed batch size of 64. In another embodiment, the CNN may be trained for another, different number of epochs, or with another, different batch size. In one embodiment, the training circuit is configured to train the CNN using backpropagation.

The training circuit is further configured to test the CNN with the remaining group. In one embodiment, the training circuit may further test the CNN using the held-out testing set.

The training circuit is further configured to determine if all the patients of the training dataset have been used for training the CNN and testing the CNN. Upon determining that all the patients have been used for training the CNN, the training circuit is configured to end the training. In one embodiment, the training circuit may end the training upon determining that a threshold percentage or proportion of patients have been used for training and testing the CNN. In another embodiment, the training circuit may end the training upon determining that threshold level of accuracy has been achieved by the CNN, or upon determining that training progress has slowed to a threshold level.

In one embodiment of apparatus 500, the set of circuits 540 further includes a display circuit. The display circuit may control the CADx system to display the digitized WSI or the probability that the patient has heart failure on a computer monitor, a smartphone display, a tablet display, or other displays. Displaying the digitized WSI or the probability that the patient has heart failure may also include printing the WSI or the probability that the patient has heart failure. The display circuit may also control the CADx to display an image of the ROI or of an input patch. The display circuit may also control the CADx system to display operating parameters or characteristics of the CNN, during both training and testing and clinical operation. Displaying the digitized WSI involves changing the character of the information present in a biopsy sample (e.g. biological tissue), to a WSI, changing the information present in the WSI to information in the digitized WSI, and then to information suitable for display on, for example, a computer monitor, a smartphone display, a tablet display, or other displays.

Figure 6:
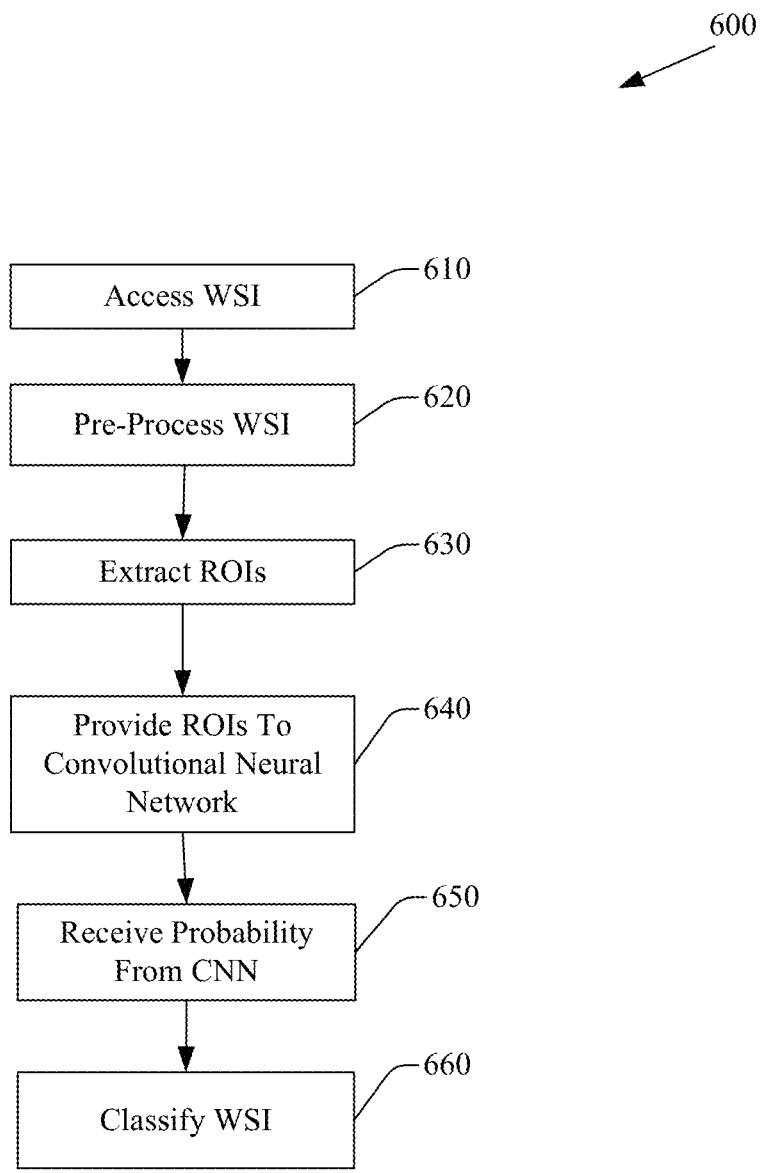
FIG. 6 illustrates an example method for predicting heart failure.

FIG. 6 illustrates a computerized method 600 for predicting heart failure. Method 600 includes, at 610, accessing a digitized whole slide image (WSI) of cardiovascular histopathology. Accessing a digitized WSI includes acquiring electronic data, reading from a computer file, receiving a computer file, reading from a computer memory, or other computerized activity. In one embodiment, the volume illustrated in the WSI is associated with H&E stained tissue derived from a transplant, an explant, a surgical tissue sample, or an endomyocardial biopsy of a patient demonstrating pathology associated with heart failure. The WSI may be acquired at 20× magnification. In other embodiments, different types of tissue acquired by different procedures may be imaged using different imaging techniques.

Method 600 also includes, at 620, generating a preprocessed WSI by downsampling the WSI. In one embodiment, downsampling the WSI includes downsampling the WSI to an apparent magnification of 5×. In another embodiment, downsampling the WSI may include downsampling the WSI to another, different apparent magnification. Preprocessing the WSI may further include color normalization, noise reduction, smoothing, or edge amplification.

Method 600 also includes, at 630, extracting a set of non-overlapping regions of interest (ROIs) from the preprocessed WSI. In one embodiment, the set of non-overlapping ROIs has an odd cardinality. In this embodiment, the set of non-overlapping ROIs is selected randomly from the WSI. In another embodiment, the set of non-overlapping ROIs may be selected non-randomly, or according to a pattern. In one embodiment, the set of non-overlapping ROIs includes 11 non-overlapping ROIs. In another embodiment, the set of non-overlapping ROIs includes another, different number of non-overlapping ROIs. In one embodiment, a member of the set of non-overlapping ROIs has dimensions of 256 pixels by 256 pixels. In another embodiment, a member of the set of non-overlapping ROIs may have other, different dimensions. The ROI dimensions may be user adjustable.

Method 600 also includes, at 640, providing the set of non-overlapping ROIs to a deep learning convolutional neural network (CNN). Providing the set of non-overlapping ROIs includes acquiring electronic data, reading from a computer file, receiving a computer file, reading from a computer memory, or other computerized activity. In one embodiment, the CNN accepts one-hundred 64 pixel by 64 pixel input patches per member of the set of non-overlapping ROIs. In another embodiment, another, different number of input patches per member of the set of non-overlapping ROIs may be provided to the CNN. In another embodiment, the input patches may have different dimensions. For example, an input patch may have dimensions of 32 pixels by 32 pixels, or 128 pixels by 128 pixels. In one embodiment, input patch dimensions may be user selectable.

In one embodiment, the CNN is a seven-layer CNN. The CNN, including a seven layer CNN, has alternating convolutional, activation, batch normalization, and convolutional fully connected layers. For example, in one embodiment, the CNN includes a first layer comprising a convolutional layer, a batch normalization layer, and an activation layer. In this embodiment, the convolutional layer has a kernel of 3, a stride of 1, and an output of 16.

In this embodiment, the CNN includes a first layer comprising a convolutional layer, a batch normalization layer, and an activation layer. In this embodiment, the convolutional layer has a has 16 kernels of size 3 and uses a stride of 1.

In this embodiment, the CNN also includes a second layer comprising a convolutional layer, a batch normalization layer, and an activation layer. In this embodiment, the convolutional layer has 16 kernels of size 2, and uses a stride of 2.

In this embodiment, the CNN also includes a third layer comprising a convolutional layer, a batch normalization layer, and an activation layer. In this embodiment, the convolutional layer has 16 kernels of size 3, with a stride of 1.

In this embodiment, the CNN also includes a fourth layer comprising a convolutional layer, a batch normalization layer, and an activation layer. In this embodiment, the convolutional layer has 16 kernels of size 3, with a stride of 2.

In this embodiment, the CNN also includes a fifth layer comprising a convolutional layer, a batch normalization layer, and an activation layer. In this embodiment, the convolutional layer has a 16 kernels of size 3, with a stride of 1.

In this embodiment, the CNN also includes a sixth layer comprising a convolutional layer, a batch normalization layer, and an activation layer. In this embodiment, the convolutional layer has 16 kernels of size 4, and uses a stride of 2.

In this embodiment, the CNN further includes a fully connected layer. The fully connected layer has a kernel of 5 and an output of 2. In another embodiment, the CNN may have other numbers of layers. In another embodiment, other kernels, strides, or outputs may be employed.

Method 600 also includes, at 650, receiving, from the CNN, a probability that a member of the set of non-overlapping ROIs is a non-failure ROI, or a failure/abnormal pathology ROI. In one embodiment, an ROI with a probability of failure p(fal)>0.50 is classified as failing.

Method 600 further includes, at 660, controlling a computer assisted diagnosis (CADx) system to classify the region of tissue represented in the WSI as a non-failure histopathology or as a failure/abnormal pathology histopathology based, at least in part, on the probabilities associated with members of the set of non-overlapping ROIs. In one embodiment, the CADx system classifies the region of tissue based on a majority vote of the probabilities associated with members of the set of non-overlapping ROIs. For example, in an embodiment in which eleven ROIs are provided to the CNN, if the CNN returns probabilities such that ten of the eleven ROIs are classified as failure/abnormal, the majority vote would indicate that the region of tissue is failure/abnormal.

Improved identification of patients with heart failure using deep learning CNNs with a sensitivity of 99% and a specificity of 93% may produce the technical effect of improving treatment efficacy by increasing the accuracy of and decreasing the time required to identify patients with heart failure. Treatments and resources may be more accurately tailored to patients with a likelihood of benefiting from said treatments and resources, so that more appropriate treatment protocols may be employed.

Using a more appropriately modulated treatment may lead to less aggressive therapeutics being required for a patient or may lead to avoiding or delaying a biopsy, a resection, or other invasive procedure. When patients experiencing heart failure are more quickly and more accurately distinguished, patients most at risk may receive a higher proportion of scarce resources (e.g., therapeutics, physician time and attention, hospital beds) while those less at risk may be spared unnecessary treatment, which in turn spares unnecessary expenditures and resource consumption. Example methods, apparatus, and other embodiments may thus have the additional effect of improving patient outcomes compared to conventional approaches.

While FIG. 6 illustrates various actions occurring in serial, it is to be appreciated that various actions illustrated in FIG. 6 could occur substantially in parallel. By way of illustration, a first process could involve pre-processing a WSI, a second process could involve extracting a set of non-overlapping ROIs, and a third process could involve providing ROIs to a CNN. While three processes are described, it is to be appreciated that a greater or lesser number of processes could be employed and that lightweight processes, regular processes, threads, and other approaches could be employed.

Figure 7:
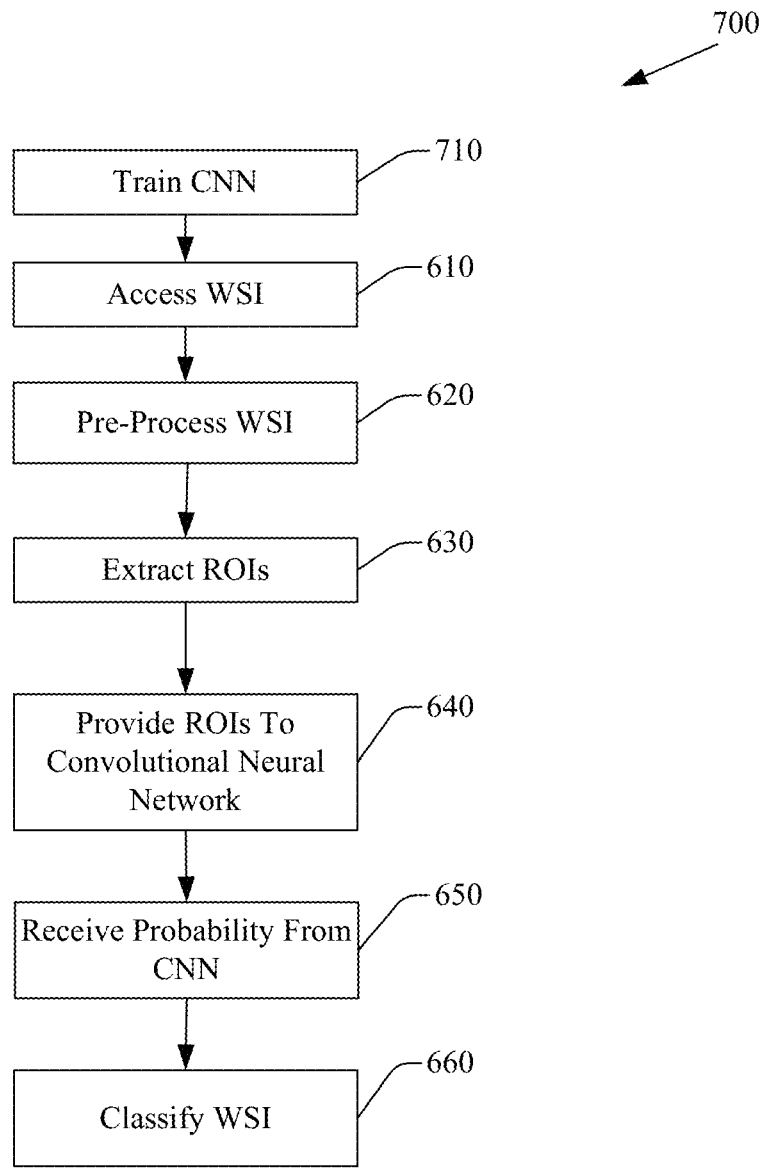
FIG. 7 illustrates an example method for predicting heart failure.

FIG. 7 illustrates an example method 700 that is similar to method 600 but includes additional elements. Method 700 includes the elements of method 600, but also includes, at 710, training the CNN.

Figure 8:
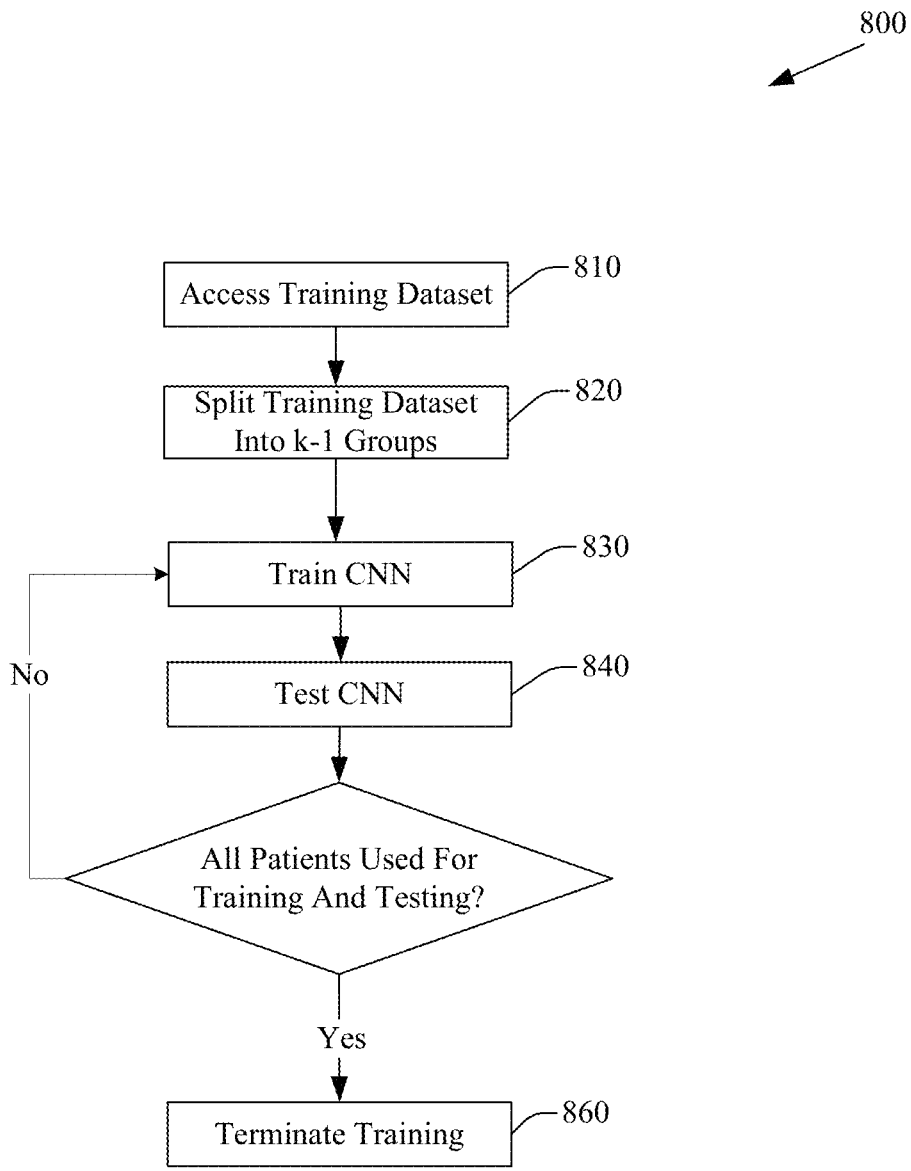
FIG. 8 illustrates an example method for training a convolutional neural network to predict heart failure.

FIG. 8 illustrates an example method 800 for training a CNN employable by embodiments described herein, including apparatus 500 or method 700. Method 800 includes, at 810, accessing a training dataset of WSIs. In one embodiment, the WSIs are acquired at 20× magnification. The training dataset includes a first subset of WSIs of H&E stained tissue acquired from patients demonstrating clinically diagnosed heart failure, and a second, disjoint subset of WSIs of tissue acquired from patients that have not been clinically diagnosed with heart failure. In one embodiment, the first subset is acquired from heart failure patients receiving a heart transplant or LVAD. Tissue acquired from the first subset may be acquired post-explant, or may be acquired as surgical core samples for patients receiving LVAD. In this embodiment, the second subset is acquired from organ donors without a history of heart failure, but where the heart was not used for transplant. Members of the training dataset may be downsampled to an apparent magnification of 5×. Accessing the training dataset of WSIs includes acquiring electronic data, reading from a computer file, receiving a computer file, reading from a computer memory, or other computerized activity.

Method 800 also includes, at 820, splitting the training dataset into k−1 groups, where k is an integer. In this embodiment, three-fold cross validation is employed. In other embodiments, other forms of cross validation may be employed.

Method 800 also includes, at 830, training the CNN with the first k−1 groups. Training the CNN includes extracting 64 pixel by 64 pixel RGB image patches from an ROI randomly selected from a member of the first k−1 groups of WSIs, where a patch has a label corresponding to the cohort to which the patient belongs (e.g. failing or non-failing). The CNN is trained using one-hundred patches per ROI. In one embodiment, the training data set is augmented by rotating a patch by ninety degrees. In another embodiment, a patch may be rotated another, different number of degrees. In one embodiment, the CNN is trained per fold for thirty epochs using stochastic gradient descent with a fixed batch size of 64. In another embodiment, the CNN may be trained for another, different number of epochs, or with another, different batch size.

Method 800 also includes, at 840, testing the CNN with the remaining group. In one embodiment, the CNN may be further tested using a held-out test group. In another embodiment, other groups may be used to test the CNN.

Method 800 further includes, at 850 determining if all the patients of the training dataset have been used for training the CNN and testing the CNN. Upon determining that all the patients have been used for training the CNN, the training is terminated at 860. In another embodiment, training may be terminated upon meeting another, different condition.

In one example, a method may be implemented as computer executable instructions. Thus, in one example, a computer-readable storage medium may store computer executable instructions that if executed by a machine (e.g., computer) cause the machine to perform methods described or claimed herein including method 600, method 700, and method 800. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 9:
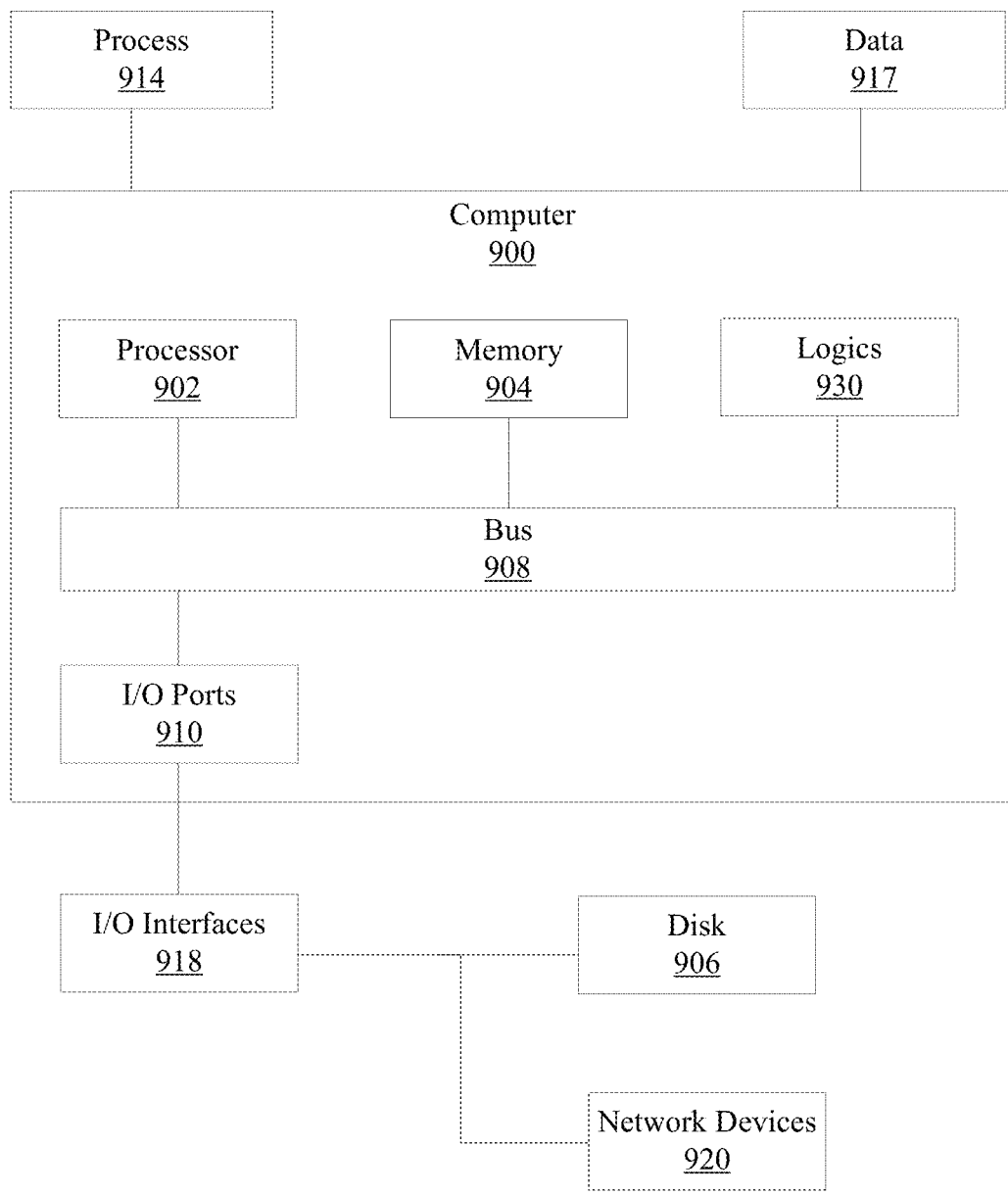
FIG. 9 illustrates an example computer in which example methods and apparatus described herein may operate.

FIG. 9 illustrates an example computer 900 in which example methods illustrated herein can operate and in which example methods, apparatus, circuits or logics may be implemented. In different examples, computer 900 may be part of a digital WSI system, may be operably connectable to a digital WSI system, or may be part of a CADx system.

Computer 900 includes a processor 902, a memory 904, and input/output (I/O) ports 910 operably connected by a bus 908. In one example, computer 900 may include a set of logics 930 that perform a method of identifying heart failure in patients using a deep learning CNN. Thus, the set of logics 930, whether implemented in computer 900 as hardware, firmware, software, and/or a combination thereof may provide means (e.g., hardware, firmware, circuits) for identifying or predicting heart failure or abnormal tissue pathology in a patient using WSIs of tissue acquired from the patient, and a CNN. In different examples, the set of logics 930 may be permanently and/or removably attached to computer 900.

Processor 902 can be a variety of various processors including dual microprocessor and other multi-processor architectures. Processor 902 may be configured to perform steps of methods claimed and described herein. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a flash memory card, or a memory stick. Furthermore, disk 906 may include optical drives like a CD-ROM or a digital video ROM drive (DVD ROM). Memory 904 can store processes 914 or data 917, for example. Disk 906 or memory 904 can store an operating system that controls and allocates resources of computer 500.

Bus 908 can be a single internal bus interconnect architecture or other bus or mesh architectures. While a single bus is illustrated, it is to be appreciated that computer 900 may communicate with various devices, circuits, logics, and peripherals using other buses that are not illustrated (e.g., PCIE, SATA, Infiniband, 1394, USB, Ethernet).

Computer 900 may interact with input/output devices via I/O interfaces 918 and input/output ports 910. Input/output devices can include, but are not limited to, digital whole slide scanners, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks, including the cloud.

Examples herein can include subject matter such as an apparatus, a CADx system, a processor, a system, a method, means for performing acts or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting heart failure according to embodiments and examples described.

One example embodiment includes a computer-readable storage device storing computer-executable instructions that, in response to execution, cause a computer assisted diagnosis (CADx) system or processor to perform operations. The operations include accessing a digitized WSI of H&E stained cardiovascular histopathology acquired at 20× magnification. The digitized WSI may be associated with a patient.

The operations further include generating a pre-processed WSI by downsampling the WSI to 5× apparent magnification.

The operations further include extracting a set of eleven non-overlapping regions of interest (ROIs) from the pre-processed WSI. In this embodiment, a member of the set of eleven non-overlapping ROIs has dimensions of 256 pixels by 256 pixels.

The operations further include providing the set of eleven non-overlapping ROIs to an unsupervised deep learning CNN configured to accept one-hundred 64 pixel by 64 pixel patches from a member of the set of eleven non-overlapping ROIs. In this embodiment, the CNN is a seven-layer CNN having less than 14000 (fourteen thousand) neurons. In this embodiment, the CNN is trained using three-fold cross validation using a training dataset of WSIs of left ventricular tissue acquired from at least 200 patients. The at least 200 patients include a first cohort diagnosed with end-stage heart failure, and a second, different cohort without heart failure. A WSI associated with the first cohort is labeled as failure/abnormal, and a WSI associated with the second cohort is labeled as non-failure. In one embodiment, the CNN is further tested on a held-out testing dataset.

The operations further include receiving, from the CNN, an image-level probability that a member of the set of eleven non-overlapping ROIs is a failure/abnormal pathology ROI.

The operations further include controlling a CADx system or processor to compute a patient-level probability that the region of tissue represented in the WSI is non-failure failure/abnormal histopathology based. The patient-level probability is based, at least in part, on a majority vote of the probabilities associated with members of the set of non-overlapping ROIs. The operations may further include controlling a CADx system or a processor to predict clinical heart failure in the patient associated with the digitized WSI based, at least in part, on the majority vote.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An apparatus for predicting heart failure, the apparatus comprising:
    a processor;
    a memory that stores a digital whole slide image (WSI) of a region of tissue derived from a heart transplant, an explant, a surgical tissue sample, or an endomyocardial biopsy, where the digital WSI has a plurality of pixels, and where a pixel has an intensity or a red-green-blue (RGB) color value;
    an input/output (I/O) interface;
    a set of circuits comprising a pre-processing circuit, an image acquisition circuit, a deep learning circuit, and a classification circuit; and
    an interface to connect the processor, the memory, the I/O interface and the set of circuits:
    where the pre-processing circuit is configured to generate a pre-processed WSI by downsampling the digital WSI;
    where the image acquisition circuit is configured to randomly select a set of non-overlapping regions of interest (ROI)s from the pre-processed WSI, and configured to provide the set of non-overlapping ROIs to the deep learning circuit, where the set of non-overlapping ROIs has an odd cardinality;
    where the deep learning circuit is configured to generate an image-level probability that a member of the set of non-overlapping ROIs is a failure/abnormal pathology ROI, where the deep learning circuit provides the member of the set of non-overlapping ROIs to a convolutional neural network (CNN), and where the CNN produces the image-level probability based, at least in part, on the member of the set of non-overlapping ROIs; and
    where the classification circuit is configured to generate a patient-level probability that the patient from which the region of tissue represented in the WSI was acquired is experiencing failure or non-failure based, at least in part, on the image-level probability.

2. The apparatus of claim 1, where the set of non-overlapping ROIs extracted by the image acquisition circuit includes eleven non-overlapping ROIs, and where a member of the set of non-overlapping ROIs has dimensions of 256 pixels by 256 pixels.

3. The apparatus of claim 1, where the WSI is an hematoxylin and eosin (H&E) stained WSI acquired at a 20× magnification.

4. The apparatus of claim 3, where the pre-processing circuit downsamples the WSI to an apparent magnification of 5×.

5. The apparatus of claim 1, where the deep learning circuit includes a CNN configured to accept one-hundred 64 pixel by 64 pixel input patches per member of the set of non-overlapping ROIs.

6. The apparatus of claim 5, where the CNN is a seven-layer CNN comprising:
    a first layer comprising a convolutional layer, a batch normalization layer, and an activation layer, the convolutional layer having 16 kernels of size 3, with a stride of 1;
    a second layer comprising a convolutional layer, a batch normalization layer, and an activation layer, the convolutional layer having 16 kernels of size 2, and a stride of 2;
    a third layer comprising a convolutional layer, a batch normalization layer, and an activation layer, the convolutional layer having 16 kernels of size 3, and a stride of 1;
    a fourth layer comprising a convolutional layer, a batch normalization layer, and an activation layer, the convolutional layer having 16 kernels of size 3, and a stride of 2;
    a fifth layer comprising a convolutional layer, a batch normalization layer, and an activation layer, the convolutional layer having 16 kernels of size 3, and a stride of 1;
    a sixth layer comprising a convolutional layer, a batch normalization layer, and an activation layer, the convolutional layer having 16 kernels of size 4, and a stride of 2; and
    a fully connected layer having a 2 kernels of size 5.

7. The apparatus of claim 5, where the classification circuit generates the patient-level probability based on a majority vote of image-level probabilities associated with members of the set of non-overlapping ROIs.

8. The apparatus of claim 7, further comprising a training circuit configured to train the CNN, where training the CNN includes:
    accessing a training dataset, where the training dataset includes a first subset of WSIs of tissue acquired from patients demonstrating clinically diagnosed heart failure, and a second, disjoint subset of WSIs of tissue acquired from patients that have not been clinically diagnosed with heart failure;
    splitting the training dataset into k−1 groups, where k is an integer;

training the CNN with the first k−1 groups;
testing the CNN with the remaining group; and
upon determining that all patients have been used for training the CNN and testing the CNN:
ending the training.

9. A non-transitory computer-readable storage device storing computer-executable instructions that when executed by a computer controls the computer to perform a method for predicting cardiac failure, the method comprising:
accessing a digitized whole slide image (WSI) of cardiovascular histopathology;
generating a pre-processed WSI by downsampling the WSI;
extracting a set of non-overlapping regions of interest (ROIs) from the pre-processed WSI, where the set of non-overlapping ROIs has an odd cardinality;
providing the set of non-overlapping ROIs to a deep learning convolutional neural network (CNN);
receiving, from the CNN, a probability that a member of the set of non-overlapping ROIs a failure/abnormal pathology ROI; and
controlling a computer assisted diagnosis (CADx) system to classify the region of tissue represented in the WSI as a non-failure histopathology or as a failure/abnormal pathology histopathology based, at least in part, on the probabilities associated with members of the set of non-overlapping ROIs.

10. The non-transitory computer-readable storage device of claim 9, where downsampling the digitized WSI includes downsampling the WSI to an apparent magnification of 5×.

11. The non-transitory computer-readable storage device of claim 9, where a member of the set of non-overlapping ROIs has dimensions of 256 pixels by 256 pixels.

12. The non-transitory computer-readable storage device of claim 9, where the set of non-overlapping ROIs is selected randomly from the WSI.

13. The non-transitory computer-readable storage device of claim 12, where the set of non-overlapping ROIs includes 11 non-overlapping ROIs.

14. The non-transitory computer-readable storage device of claim 9, where the digitized WSI represents hematoxylin and eosin (H&E) stained tissue derived from a transplant, an explant, a surgical tissue sample, or an endomyocardial biopsy.

15. The non-transitory computer-readable storage device of claim 14, where the CADx system classifies the region of tissue based on a majority vote of the probabilities associated with members of the set of non-overlapping ROIs.

16. The non-transitory computer-readable storage device of claim 14, the method further comprising training the CNN, where training the CNN includes:
accessing a training dataset, where the training dataset includes a first subset of WSIs of tissue acquired from patients demonstrating clinically diagnosed heart failure, and a second, disjoint subset of WSIs of tissue acquired from patients that have not been clinically diagnosed with heart failure;
splitting the training dataset into k−1 groups, where k is an integer;
training the CNN with the first k−1 groups;
testing the CNN with the remaining group;
upon determining that all patients represented in the training dataset have been used for training the CNN and testing the CNN:
ending the training.

17. The non-transitory computer-readable storage device of claim 9, where the CNN accepts one-hundred 64 pixel by 64 pixel input patches per member of the set of non-overlapping ROIs.

18. The non-transitory computer-readable storage device of claim 17, where the CNN is a seven-layer CNN.

19. The non-transitory computer-readable storage device of claim 18, where the CNN comprises:
a first layer comprising a convolutional layer, a batch normalization layer, and an activation layer, the convolutional layer having 16 kernels of size 3, and a stride of 1;
a second layer comprising a convolutional layer, a batch normalization layer, and an activation layer, the convolutional layer having 16 kernels of size 2, and a stride of 2;
a third layer comprising a convolutional layer, a batch normalization layer, and an activation layer, the convolutional layer having 16 kernels of size 3, and a stride of 1;
a fourth layer comprising a convolutional layer, a batch normalization layer, and an activation layer, the convolutional layer having 16 kernels of size 3, and a stride of 2;
a fifth layer comprising a convolutional layer, a batch normalization layer, and an activation layer, the convolutional layer having 16 kernels of size 3, and a stride of 1;
a sixth layer comprising a convolutional layer, a batch normalization layer, and an activation layer, the convolutional layer having 16 kernels of size 4, and a stride of 2; and
a fully connected layer having 2 kernels of size 5.

20. A computer-readable storage device storing computer-executable instructions that, in response to execution, cause a computer assisted diagnosis (CADx) system to perform operations comprising:
accessing a digitized whole slide image (WSI) of cardiovascular histopathology acquired at 20× magnification;
generating a pre-processed digitized WSI by downsampling the digitized WSI to 5× apparent magnification;
extracting a set of eleven non-overlapping regions of interest (ROIs) from the pre-processed digitized WSI, where a member of the set of eleven non-overlapping ROIs has dimensions of 256 pixels by 256 pixels;
providing the set of eleven non-overlapping ROIs to an unsupervised deep learning convolutional neural network (CNN), where the CNN accepts one-hundred 64 pixel by 64 pixel patches from a member of the set of eleven non-overlapping ROIs, where the CNN is a seven-layer CNN having less than 14000 neurons, where the CNN is trained using three-fold cross validation using a training dataset of WSIs of left ventricular tissue acquired from at least 200 patients, and where the at least 200 patients include a first cohort diagnosed with end-stage heart failure, and a second, different cohort without heart failure, where a WSI associated with the first cohort is labeled as failure/abnormal, and a WSI associated with the second cohort is labeled as non-failure;
receiving, from the CNN, an image-level probability that a member of the set of eleven non-overlapping ROIs is a failure/abnormal pathology ROI; and
computing a patient-level probability that the cardiovascular histopathology represented in the digitized WSI is non-failure failure/abnormal histopathology based, at least in part, on a majority vote of the probabilities associated with members of the set of non-overlapping ROIs.

* * * * *

UNITED STATES PATENT AND TRADEMARK OFFICE
CERTIFICATE OF CORRECTION

PATENT NO. : 10,528,848 B2  
APPLICATION NO. : 15/799129  
DATED : January 7, 2020  
INVENTOR(S) : Anant Madabhushi et al.

Page 1 of 1

It is certified that error appears in the above-identified patent and that said Letters Patent is hereby corrected as shown below:

In the Specification

Column 1, Lines 13 through 21; please replace "The invention was made with government support under grants 1U24CA199374-01, R01CA202752-01A1, R01CA208236-01A1, R21CA179327-01, R21CA195152-01, R01DK098503-02, R01HL105993, F30NS092227, and 1 C06 RR012463-01 awarded by the National Institutes of Health. Also grants W81XWH-13-1-0418, W81XWH-14-1-0323, and W81XWH16-1-0329 awarded by the Department of Defense. The government has certain rights in the invention." with --The invention was made with government support under grants DK098503, CA195152, CA179327, CA199374, NS092227, HL105993, CA202752, CA208236, and RR012463 awarded by the National Institutes of Health. Also grants W81XWH-13-1-0418, W81XWH-14-1-0323, W81XWH16-1-0329, and W81XWH-15-1-0558 awarded by the Department of Defense. The government has certain rights in the invention.--

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*